(12) United States Patent
Vitali et al.

(10) Patent No.: US 11,666,770 B2
(45) Date of Patent: Jun. 6, 2023

(54) IMPLANTABLE MEDICAL DEVICE FOR DEFIBRILLATION OF THE HEART BASED ON THE DETECTION OF MECHANICAL VIBRATIONS

(71) Applicant: SORIN CRM SAS, Clamart (FR)

(72) Inventors: Luca Vitali, Strambino (IT); Daniel Kroiss, Saint-Ismier (FR)

(73) Assignee: Sorin CRM SAS, Clamart (FR)

( * ) Notice: Subject to any disclaimer, the term of this patent is extended or adjusted under 35 U.S.C. 154(b) by 383 days.

(21) Appl. No.: 16/721,497

(22) Filed: Dec. 19, 2019

(65) Prior Publication Data

US 2020/0197714 A1 Jun. 25, 2020

(30) Foreign Application Priority Data

Dec. 20, 2018 (EP) .................................... 18306762

(51) Int. Cl.
*A61N 1/39* (2006.01)
*A61B 5/11* (2006.01)

(52) U.S. Cl.
CPC .......... *A61N 1/3956* (2013.01); *A61B 5/1126* (2013.01); *A61B 2562/0204* (2013.01); *A61B 2562/0219* (2013.01)

(58) Field of Classification Search
CPC ................ A61N 1/3956; A61B 5/1126; A61B 2562/0204; A61B 2562/0219

(Continued)

(56) References Cited

U.S. PATENT DOCUMENTS 6,440,082 B1 * 8/2002 Joo ...................... A61B 5/0538
600/509
7,277,761 B2 10/2007 Shelchuk
(Continued)

FOREIGN PATENT DOCUMENTS

JP 08-047544 A 2/1996
JP 1085344 A 4/1998
(Continued)

OTHER PUBLICATIONS

Extended European Search Report on EP Application No. 18306762.8 dated Mar. 29, 2019. 6 pages.
(Continued)

*Primary Examiner* — Carl H Layno
*Assistant Examiner* — Michael J Lau
(74) *Attorney, Agent, or Firm* — Foley & Lardner LLP

(57) ABSTRACT

The present disclosure relates to an implantable medical device, in particular a cardiac defibrillator, comprising an implantable defibrillator configured to generate an electrical defibrillation signal, an implantable electrode connected with the implantable defibrillator by a lead and configured to deliver the electrical defibrillation signal to a patient, an implantable sensor configured to detect mechanical vibrations by the heart of the patient and to provide a detection signal based on the detected mechanical vibrations, and a controller configured to analyze the detection signal to determine at least one parameter characterizing the mechanical vibrations and to initiate a defibrillation operation of the implantable defibrillator based on the determined parameter characterizing the mechanical vibrations.

11 Claims, 6 Drawing Sheets

(58) Field of Classification Search
USPC .......................................................... 607/6
See application file for complete search history.

(56) References Cited

U.S. PATENT DOCUMENTS

| | | | |
|---|---|---|---|
| 7,813,805 | B1 | 10/2010 | Farazi |
| 7,869,869 | B1 | 1/2011 | Farazi |
| 8,876,727 | B2* | 11/2014 | Zhang .................... A61B 7/005 607/42 |
| 8,996,101 | B2* | 3/2015 | Zhang .................... A61B 5/363 600/528 |
| 2004/0230243 | A1* | 11/2004 | Haefner .................. A61N 1/05 607/27 |
| 2007/0208390 | A1* | 9/2007 | Von Arx ............ A61N 1/37288 607/32 |
| 2008/0086036 | A1* | 4/2008 | Hartley .............. A61N 1/36528 607/6 |
| 2011/0071411 | A1* | 3/2011 | Shuros ............... A61N 1/36514 607/19 |
| 2011/0098587 | A1 | 4/2011 | Haefner |
| 2012/0303078 | A1 | 11/2012 | Li et al. |
| 2013/0289377 | A1* | 10/2013 | Song ....................... A61B 7/04 600/374 |
| 2015/0005588 | A1* | 1/2015 | Herken ................... G10L 25/48 600/509 |
| 2015/0196758 | A1* | 7/2015 | Stahmann .............. A61B 5/363 600/518 |
| 2017/0231505 | A1* | 8/2017 | Mahajan ................. A61B 7/00 600/484 |
| 2018/0256908 | A1 | 9/2018 | Casavant et al. |
| 2018/0280705 | A1* | 10/2018 | Maile .................. A61N 1/37211 |

FOREIGN PATENT DOCUMENTS

| | | |
|---|---|---|
| JP | 2007-503280 A | 2/2007 |
| JP | 2008-502444 A | 1/2008 |
| JP | 2008-517712 A | 5/2008 |
| JP | 2009-285506 A | 12/2009 |
| JP | 2013-535236 A | 9/2013 |
| JP | 2016-510654 A | 4/2016 |
| JP | 2017-525415 A | 9/2017 |

OTHER PUBLICATIONS

Office action issued in JP Application No. 2019-228169 dated Mar. 31, 2021.

* cited by examiner

IMPLANTABLE MEDICAL DEVICE FOR DEFIBRILLATION OF THE HEART BASED ON THE DETECTION OF MECHANICAL VIBRATIONS

CROSS-REFERENCE TO RELATED PATENT APPLICATIONS

This application claims the benefit of and priority to European Application No. 18306762.8, filed Dec. 20, 2018, which is incorporated herein by reference in its entirety.

BACKGROUND

The present disclosure relates to the field of implantable medical devices, in particular, for defibrillation of the heart of a patient, for example, for treating tachyarrhythmia.

Cardiac tachyarrhythmia represents a severe health problem from which more and more patients are suffering. In particular, patients suffering from congestive heart failure are at increased risk of tachyarrhythmias, such as atrial fibrillation (AF), ventricular tachyarrhythmias (ventricular tachycardia (VT) and ventricular fibrillation (VF)), and atrial flutter, particularly when the underlying morbidity is a form of coronary artery disease, cardiomyopathy, mitral valve prolapse, or other valvular heart disease. Sympathoadrenal activation also significantly increases the risk and severity of tachyarrhythmias due to neuronal action of the sympathetic nerve fibers in, on, or around the heart and through the release of epinephrine (adrenaline), which can exacerbate an already-elevated heart rate. VT originates solely in the lower heart in either the ventricular tissue or Purkinje fibers. During VT, electrical signals within the ventricles begin firing abnormally and cause a rapid rate of ventricular contraction; the rate is so rapid that the heart is unable to fill properly, thereby substantially reducing the forward flow, which results in dramatic reduction in the volume of blood ejected through the aortic valve into the peripheral vascular system. This sudden reduction in blood flow can have immediate deleterious consequences since the brain and other vital organ systems require adequate blood perfusion to maintain their biological integrity. When starved of blood, even for short periods of time, vital organ systems can be damaged. The brain is particularly sensitive to reduced cardiac output. Initially, during low flow conditions, such as during VT, the brain's electrical systems are affected, and patient consciousness may be compromised. If this low or no flow condition persists for minutes, brain tissue damage begins. After six to eight minutes, this damage can become permanent and may ultimately lead to chronic impairment or death, unless the hemodynamic compromise caused by the VT is immediately and definitively corrected. During the VT, action potentials circulating in the ventricles collide and interfere with the normal propagation of action potentials from the sinoatrial (SA) node and the resulting rapid heart rate causes the heart chambers to contract prematurely and without adequately filling, thus preventing proper blood flow and causing potentially lethal hemodynamic compromise. Thus, VT can present life-threatening risk and can degenerate into VF, asystole and sudden cardiac death. Both VT and VF, as well as other forms of potentially life-threatening tachyarrhythmias, must be promptly treated to restore the heart to normal sinus rhythm. The current standard of care for treating VT includes, in order of increasing medical urgency, anti-arrhythmic medications, cardioversion, radiofrequency ablation, and heart surgery. U.S. Pat. No. 7,277,761 discloses vagal stimulation for improving cardiac function in heart failure patients. An autonomic nerve is stimulated to affect cardiac function using a stimulation device in electrical communication with the heart by way of three leads suitable for delivering multi-chamber endocardial stimulation and shock therapy. Where the stimulation device is intended to operate as an implantable cardioverter-defibrillator (ICD), the device detects the occurrence of an arrhythmia, and applies a therapy to the heart aimed at terminating the detected arrhythmia. Defibrillation shocks are generally of moderate to high energy level, delivered asynchronously, and pertaining exclusively to the treatment of fibrillation. U.S. Pat. Nos. 7,813,805 and 7,869,869 both disclose sub-cardiac threshold vagus nerve stimulation. A vagus nerve stimulator is configured to generate electrical pulses below a cardiac threshold, which are transmitted to a vagus nerve, so as to inhibit or reduce injury resulting from ischemia. For arrhythmia detection, a heart stimulator utilizes atrial and ventricular sensing circuits to sense cardiac signals to determine whether a rhythm is physiologic or pathologic. In low-energy cardioversion, an ICD device typically delivers a cardioversion stimulus synchronously with a QRS complex; thus, avoiding the vulnerable period of the T-wave and avoiding an increased risk of initiation of VF. In general, if anti-tachycardia pacing or cardioversion fails to terminate a tachycardia, then, for example, after a programmed time interval or if the tachycardia accelerates, the ICD device initiates defibrillation therapy.

US 2011/0098587 discloses an ICD device using a non electrophysiologic source sensor sensing a signal independent of a cardiac electric activity, such as an acoustic signal of cardiac heart sounds, to quickly search for a signal of interest, in case no clear electric cardiac signal can be identified by a plurality of subcutaneous non-intrathoracic electrodes due to the presence of electrical noise or artifacts. A signal processor is configured to initiate a detection window at a start time determined from the use of the non-electrophysiologic signal to identify a cardiac signal from the plurality of electrical signals using the detection window.

However, one of the most critical functions in an implantable defibrillator is to ensure sensitive and specific detection of tachyarrhythmic events. Good sensitivity is required in order to provide timely delivery of shock pulses, reverting the patient to sinus rhythm as quickly as possible. At the same time it is very important that unnecessary defibrillation shocks, which are known to have several severe adverse effects, are minimized. Therefore, the implantable medical device needs to have good specificity in its detection algorithms. In the art, cardiac electrical signals (surface electrocardiogram or intracardiac electrograms) are used to discriminate between tachycardic events requiring immediate intervention and other events in which shock delivery may be delayed or even avoided at all. However, the decision on whether or not defibrillation is to be provided based on the analysis of electrical signals has not proven to be sufficiently reliable.

SUMMARY

In view of the above, it is an object of the present disclosure to provide an implantable medical device with increased sensitivity and specificity of detections of anomalous and risky arrhythmia of the heart as compared to the art.

The above-mentioned problem is addressed by an implantable medical device, in particular cardiac defibrillator, comprising an implantable defibrillator configured to generate an electrical defibrillation signal; an implantable electrode connected with the implantable defibrillator by a lead and configured to deliver the electrical defibrillation signal to a patient; a sensor means, in particular an implantable sensor means, configured to detect mechanical vibrations by the heart of the patient and to provide a detection signal based on the detected mechanical vibrations; and a controller configured to analyze the detection signal to determine at least one parameter characterizing the mechanical vibrations and to initiate a defibrillation operation of the implantable defibrillator or not based on the determined parameter/s characterizing the mechanical vibrations only.

It is to be understood that mechanical vibrations can in particular relate to the heart sounds. Detection of a heart sound may be achieved via detection of a vibration associated therewith and the detection of a heart sound may be based on an acoustical or vibration signal. According to one variant, the sensor means can be implantable sensor means or according to another variant, the sensor means is attachable to a patient's skin.

Herein, the mechanical vibrations are thus closely related to the hemodynamic activity of the heart. During a normal cycle the cardiac valves open and close rhythmically, producing characteristic vibrations, which are one of the main determinants of the heart sounds. Since the opening and closing of a cardiac valve is driven by the blood flow across the valve section, the presence of heart sounds can be associated to the existence of blood flow in the vasculature, and vice-versa the absence of heart sounds may indicate lack of blood circulation and consequently of tissue perfusion. Thus, unlike US2011/0098587, the non-electrophysiologic signal is not used to determine a time window in which the electrical cardiac signal is to be searched for, but is directly used by the controller for a reliable discrimination between situations in that it is appropriate to supply an electrical shock and situations in that no immediate action is necessary. In particular, cardiac sounds, e.g. recorded in the endocardial acceleration trace, have significantly reduced amplitudes during hemodynamically unstable ventricular tachycardia (VT) event as compared to amplitudes occurring during sinus rhythm or hemodynamically stable VT episodes (see detailed description of FIG. 1 below). Thus, based on the analysis of the amplitudes of cardiac sounds, particularly, in the endocardial acceleration trace, the operation of the implantable defibrillator may be controlled. Whereas the absence of a non-electrophysiologic signal in US 2011/0098587 would indicate that the electric signal sensed relates to electric noise, the absence of such signal according to the invention would trigger a defibrillation action as it relates to an insufficient contraction of the heart of a patient.

The controller is moreover configured to control the operation of the implantable defibrillator based on no additional detection signal, in particular, no electrical cardiac signal. Thus, the operation of the implantable defibrillator is based solely on the at least one parameter characterizing the mechanical vibrations. The operation of the implantable defibrillator in this embodiment is controlled based on the analysis of the detected sound signal only.

According to an embodiment, the determined parameter can be at least one of amplitude, correlation, in particular autocorrelation, morphology, e.g. the presence of doublets in the detected signal. If, for example, the amplitudes of the sound signals fall below a predetermined first threshold, a defibrillation signal may be delivered to the patient. Here morphology relates to the shape of the signal, e.g. the width of the signal, the presence of doublets, etc.

The vibrations generated by the heart can be detected and measured by a suitable sensor and the information contained in the signal can be processed and made available for several purposes. The sensor means can be positioned in the lead, so that in use it will be in or close to the heart, or separate from the lead, e.g. in a housing comprising the controller. For example, the implantable sensor means may comprise an acoustic sensor, for obtaining a detected acoustic signal, and/or an accelerometer for obtaining an accelerometer signal.

In all of the above-described embodiments the analysis of the detection signal may comprise extracting an envelope of the detection signal, for example, obtained by an accelerometer or and using the extracted envelope as a parameter characterizing the mechanical vibrations. For example, the controller may be configured to cause the defibrillator to deliver the electrical defibrillation signal to the patient, if the parameter characterizing the mechanical vibrations, in particular the extracted envelope, for example, the envelope of an accelerometer signal, is below a predetermined threshold, e.g. the first predetermined threshold, see also detailed description below. Thresholding can be considered a reliable means for facilitating the determination whether or not a therapeutic shock has to be delivered. Instead of the detection signal itself an extracted envelope of the same or a parameter based on a correlation value of the detection signal may be used for comparison with the threshold (see also below). The morphology, e.g. the width of the signal or the presence of doublets of the signal can also deliver the necessary information.

In all of the above-described embodiments more than one sensor means configured to detect a heart sound may be provided, for example, at least one additional sensor means configured to detect mechanical vibrations and to provide an additional detection signal may be positioned in the lead. Two or more sensor means configured to detect mechanical vibrations may be positioned in the lead at different positions. The controller may be configured to control the operation of the defibrillator based on the additional detection signal obtained by the additional sensor means. In this case, the controller may be configured to control the operation of the defibrillator based on a correlation between the detection signal and the additional detection signal and/or a signal to noise ratio of the detection signal and the additional detection signal as a parameter characterizing the mechanical vibrations, in order to even further increase sensitivity and specificity.

According to a further embodiment, the controller can be configured to analyze the detection signal obtained after a first electrical defibrillation signal has been delivered to the patient and to control operation of the implantable defibrillator based on the detection signal such that a second electrical defibrillation signal is delivered or not to the patient based on the analyzed detection signal. For example, based on the analyzed detection signal, it can be determined whether or not after a therapeutic shock delivered by the defibrillator and the electrode to the patient unstable ventricular tachycardia (VT) or ventricular fibrillation (VF) has terminated. If no termination of the unstable VT or VF has been achieved, the controller may cause the defibrillator to deliver another therapeutic shock. Otherwise unnecessarily delivering an additional shock can be avoided.

BRIEF DESCRIPTION OF DRAWINGS

Additional features and advantages of the present disclosure will be described with reference to the drawings. In the description, reference is made to the accompanying figures that are meant to illustrate preferred embodiments of the disclosure. It is understood that such embodiments do not represent the full scope of the disclosure.

DETAILED DESCRIPTION

Figure 1:
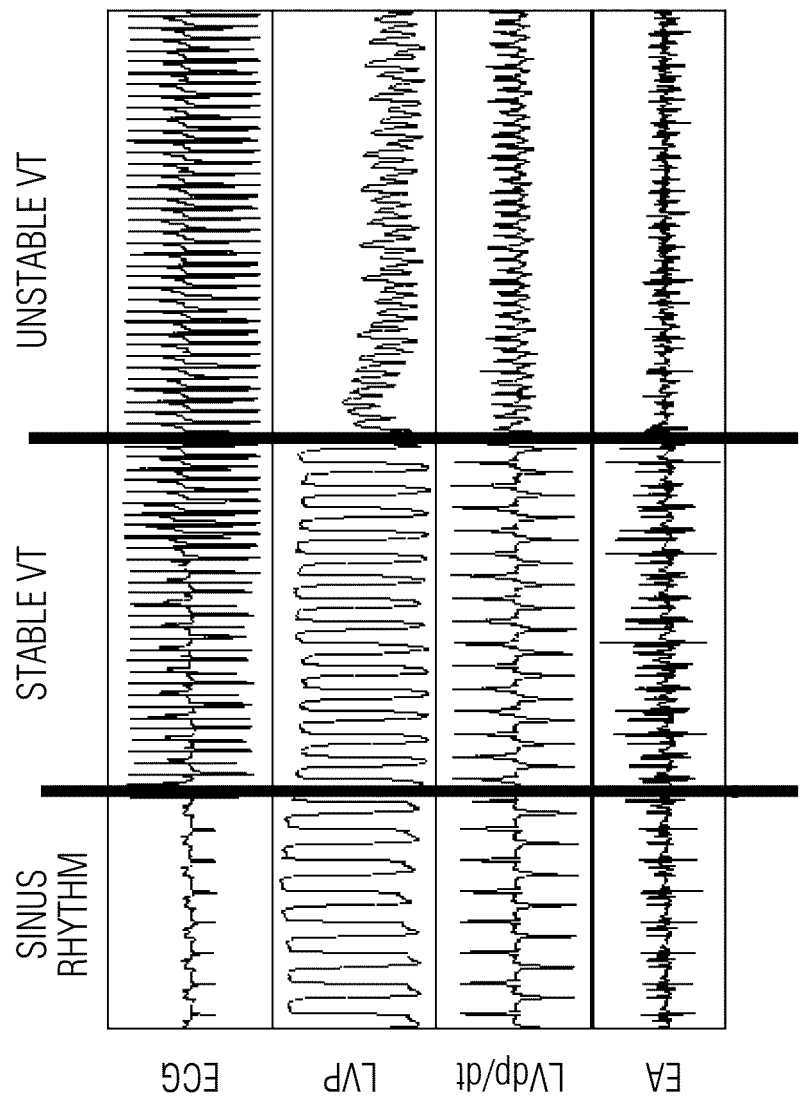
FIG. 1 illustrates left ventricle pressure and the rate of left ventricle pressure rise for a sinus rhythm, stable ventricular tachycardia and unstable ventricular tachycardia and corresponding detection signals.

The present disclosure will now be described with reference to the attached figures. Various structures, systems and devices are schematically depicted in the drawings for purposes of explanation only and so as to not obscure the present disclosure with details which are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary or customary meaning as understood by those skilled in the art, is intended to be implied by consistent usage of the term or phrase herein unless explicitly stated otherwise.

The following embodiments are described in sufficient detail to enable those skilled in the art to make use of the disclosure. It is to be understood that other embodiments would be evident, based on the present disclosure, and that system, structure, process or mechanical changes may be made without departing from the scope of the present disclosure. In the following description, numeral-specific details are given to provide a thorough understanding of the disclosure. However, it would be apparent that the embodiments of the disclosure may be practiced without the specific details. In order to avoid obscuring the present disclosure, some well-known circuits, system configurations, structure configurations and process steps are not disclosed in detail.

Herein, it is disclosed an implantable medical device that is capable of delivering a therapeutic electrical signal in response to the detection of an event. The event can be unstable ventricular tachycardia (VT) or ventricular fibrillation (VF). The event is detected based on mechanical vibrations associated with heart sounds. In general, the effectiveness of cardiac contraction can be determined by detecting the mechanical vibrations of heart sounds.

FIG. 1 shows characteristics of a sinus rhythm, stable VT and unstable VT, respectively. In the upper row an electrocardiac signal is shown. Whereas the electrocardiac signal significantly differs in the stable and unstable VT regimes from the sinus rhythm, a reliable differentiation between stable and unstable VT is not possible based on the electrocardiac signal. The left ventricle pressure and the rate of left ventricle pressure rise for the sinus rhythm, stable ventricular tachycardia and unstable ventricular tachycardia are shown in the second and third row of FIG. 1. As can be seen almost no blood flow is present in the unstable VT regime. This can be used to detect unstable VT based on the detection of heart noise. As can be seen in the lowest row of FIG. 1, cardiac sounds recorded in the EA trace are significantly reduced in the unstable VT regime as compared to the stable VT and sinus rhythm regimes. In principle, cardiac sounds may be analyzed in order to detect an event that requires for an electric shock to be delivered to a patient based on parameters as the first cardiac sound (S1) complex amplitude, second cardiac sound (S2) complex amplitude, S1 and/or S2 timing, in relation to one another or another sound complex presence (S3, S4).

Thus, based on the detection of mechanical vibrations a therapeutic electrical signal may be delivered. For example, a cardiac defibrillator implanted into the patient is activated. In addition, reversion to sinus rhythm (or other hemodynamically stable situation) after delivery of a shock may be confirmed based on detected mechanical vibrations related to the heart sounds. Thereby, it can be avoided to deliver another shock in case of doubtful interpretation of the situation, or the delivery of another shock may be accelerated in case the first one was ineffective to restore sinus rhythm, or if the VT degenerated from the stable to the unstable regime.

Figure 2:
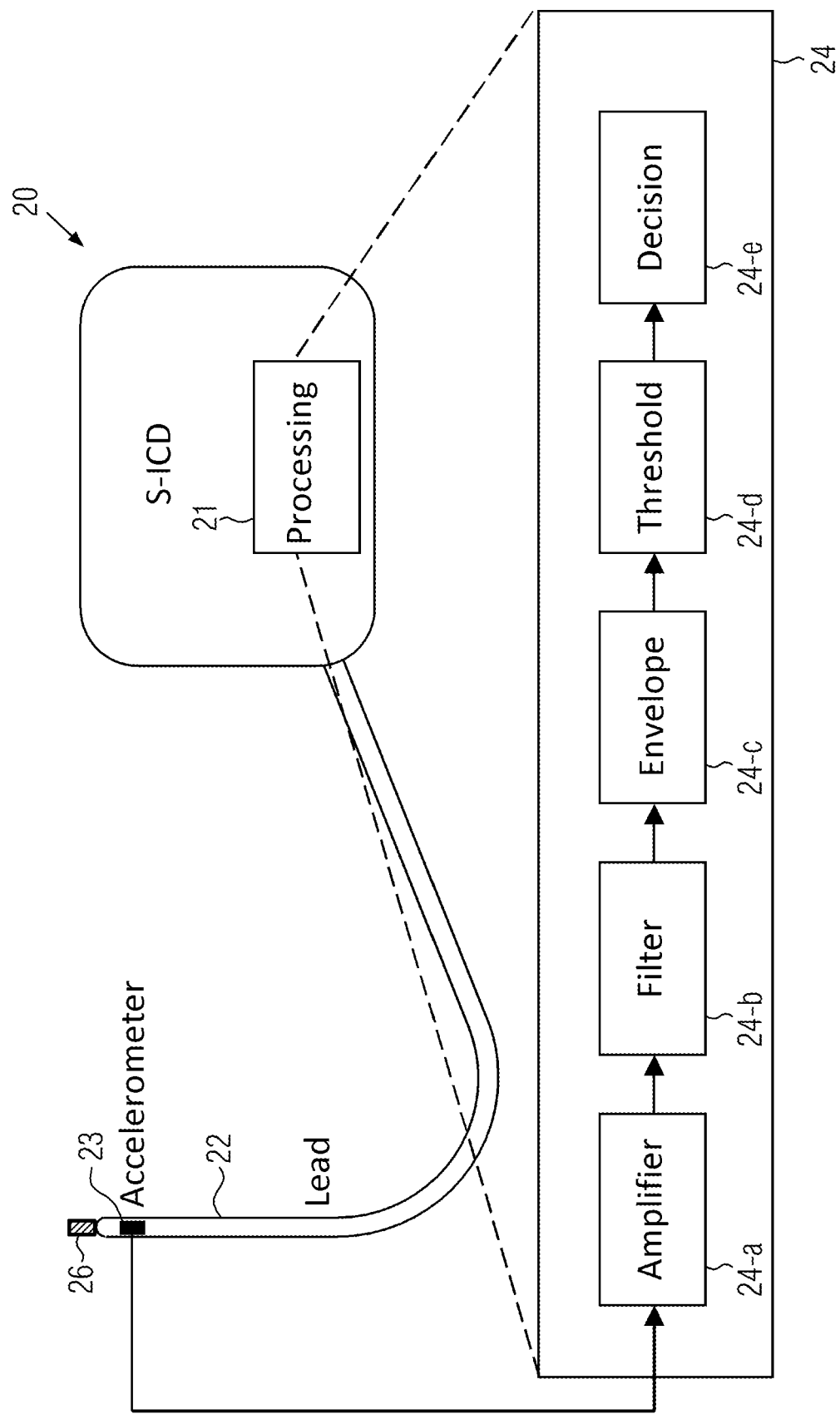
FIG. 2 shows a configuration of an implantable medical device comprising a single sensor means, in particular, an accelerometer, for detecting a heart sound in accordance with an example of the present invention.

FIG. 2 shows an implantable medical device in form of subcutaneously implantable cardiac defibrillator (S-ICD) in accordance with an embodiment of the present disclosure. The device comprises a defibrillator unit 20 and a controller 21, also called data processing unit.

The defibrillator 20 may include an electrical pulse generator that is tuned to improve autonomic regulatory function by triggering action potentials that propagate both afferently and efferently within a nerve. The defibrillator unit 20 may be enclosed in a hermetically sealed housing constructed of a biocompatible material, such as titanium. The housing may contain electronic circuitry powered by a battery, such as a lithium carbon mono fluoride primary battery or a rechargeable secondary cell battery.

The electronic circuitry may be implemented using complementary metal oxide semiconductor integrated circuits that may include a voltage regulator that regulates system power, logic and control circuitry, including a recordable memory within which the defibrillation parameters are stored, that controls overall pulse generator function, receives and implements programming commands from the external programmer, or other external source, collects and stores telemetry information, processes sensory input, and controls scheduled and sensory-based therapy outputs, a transceiver that remotely communicates with the external programmer using radio frequency signals, an antenna, which receives programming instructions and transmits the telemetry information to the external programmer, and a reed switch or other means of detecting the presence of a magnet, that provides remote access to the operation of the defibrillator 20 using an external programmer, a simple patient magnet, or an electromagnetic controller.

The data processing unit/controller 21 is configured to execute a control program according to stored defibrillation parameters and timing cycles. An electrode 26 is connected via a lead 22 to the defibrillator 20. The electrode 26 may be provided in a variety of forms, such as, e.g., a helical electrode, probe electrode, cuff electrode. A pair of such electrodes may be provided. According to an example, the housing of the defibrillator 20 can function as a return electrode. In operation, the electrode 26 may be placed subcutaneously over the sternum, while the defibrillator 20 may be implanted laterally in a subcutaneous pocket. The electrode 26 may be attached to a vagus nerve of the patient.

In the example shown in FIG. 2 a sensor means 23 is located in the lead 22. The sensor means 23 can be an accelerometer or an acoustic sensor for detecting mechanical vibrations coming from the heart and impinging on the sternum and transmitted to the lead. The sensor means 23 provides a detection signal based on the detected vibrations. The detection signal can be processed (analyzed) by means of the data processing unit/controller 21 provided in the defibrillator 20 to determine at least one parameter representative of the mechanical vibrations. Processing of the detection signal may be performed at least partly in the frequency domain, i.e., the detection signal undergoes some time-frequency processing, for example, by means of a (moving window) FFT or wavelet transform. In the embodiment shown in FIG. 2 the data processing unit/controller 21 comprises an amplifier means 24-*a* with constant or variable gain, filtering means 24-*b* with time constant or time adjustable filter coefficients, envelope extraction means 24-*c*, thresholding means 24-*d* and a decision means 24-*e*.

The amplifier means 24-*a* (for example, coupled with a powering or biasing circuitry to activate the sensor means 23) amplifies the detection signal obtained by the sensor means 23. The filtering means 24-*b* may comprise a bandpass filter. The envelope extraction means 24-*c* extracts an envelope of the detection signal thereby facilitating the subsequently performed thresholding process. A (full wave) rectifier means may be provided upstream of the envelope extraction means 24-*c* in order to convert negative peaks in positive ones or vice versa. The extracted envelope is compared to a predetermined threshold by the thresholding means 24-*d*.

Based on the comparison result the decision means 24-*e* causes action of the defibrillator 20, i.e., deliverance of a therapeutic electrical signal to the patient, or not. In particular, the decision means 24-*e* causes the defibrillator 20 to deliver an electrical shock in order to terminate supposed hemodynamically unstable tachycardia or a ventricular fibrillation, if the extracted envelope falls below the predetermined threshold. In this case, the heart is not properly pumping blood into the vasculature. The predetermined threshold may be fixed or may be dynamically adjustable. In particular, the threshold level may be proportional to a certain property of the detection signal, may be dynamically evaluated (such as for example the power averaged over a certain time window), may have a fixed or variable offset with respect to a baseline, a noise level or another parameter of the detection signal that is dynamically evaluated, The threshold might be forced to be comprised within one or two limits (clamping) and it might be calculated from the raw accelerometer signal, or from the accelerometer signal processed in a different way (e.g. with a different filter) than the signal that is compared to the threshold.

The thresholding means 24-*d* may employ a hysteresis and may have a delay such that, once a low-to-high transition is done, a high-to-low transition may not occur before a predetermined time. This could be useful to merge several transitions, so that a continuous high level, rather than a series of pulses, might be generated when the heart is performing well, while a continuous low level might be generated in the absence of blood circulation. The thresholding means 24-*d* may also employ some hold-off period, i.e. a predetermined period of time after the end of a pulse before a new pulse can be generated.

The decision means 24-*e* provides an output based on the detection signal provided by the sensor means 23 alone. As an example, the accelerometer or acoustic sensor information could be integrated with information related to the presence (or absence) of discernible electrocardiogram complexes.

Figure 3:
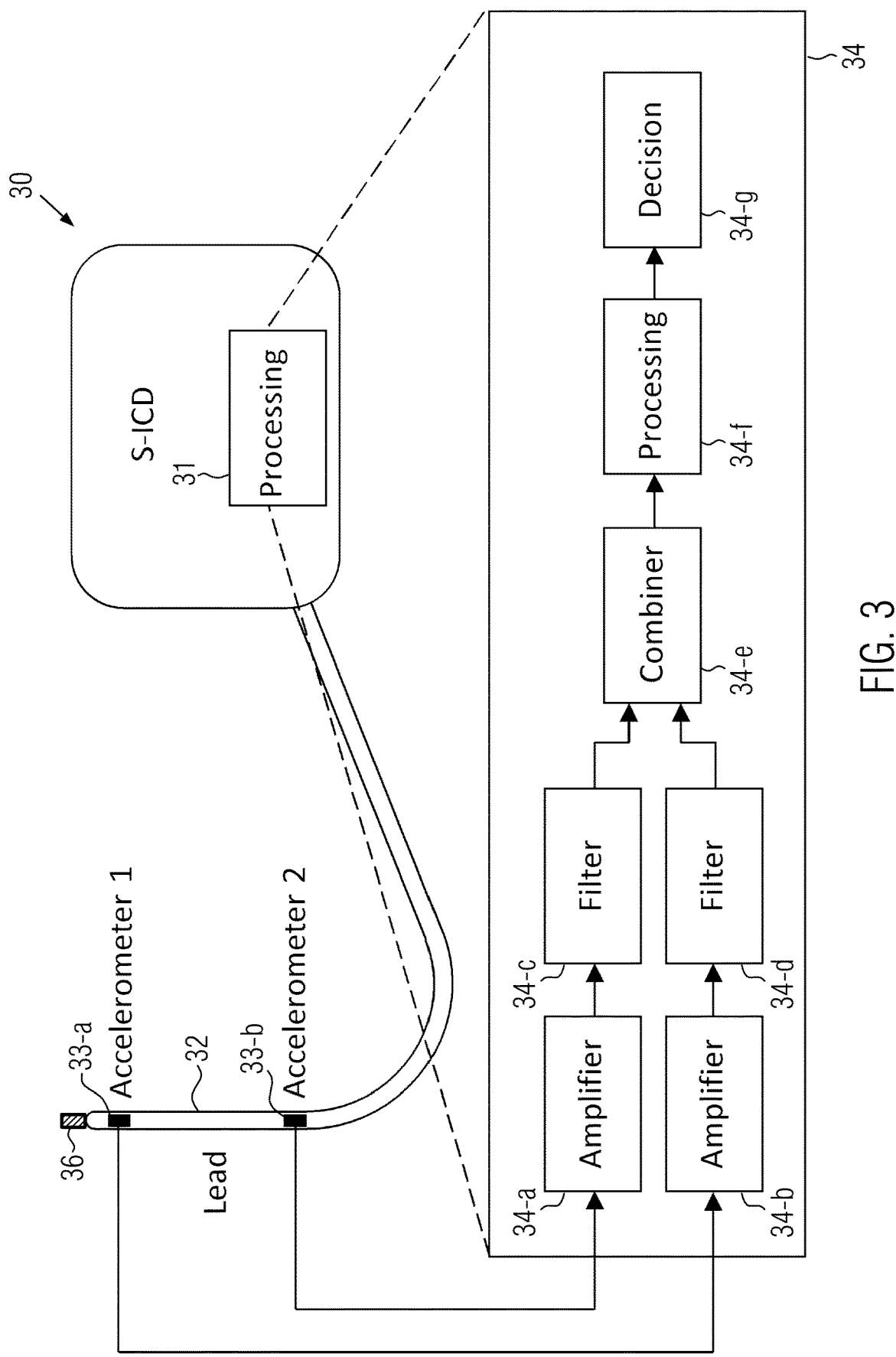
FIG. 3 shows a configuration of an implantable medical device comprising two sensor means, in particular, two accelerometers, for detecting a heart sound in accordance with an example of the present invention.

FIG. 3 shows a device similar to the one shown in FIG. 2 but including two sensor means 33-*a* and 33-*b* that are provided in a lead 32 connecting an electrode 36 to defibrillator 30. The defibrillator 30 comprises a processing means/controller 31 that comprises two amplifier means 34-*a* and 34-*b* with constant or variable gain for amplifying the detection signals provided by the two sensor means 33-*a* and 33-*b*, two filtering means 34-*c* and 34-*d* with time constant or time adjustable filter coefficients for filtering the amplified detection signals, a combiner means 34-*e* for combining the amplified and filtered detection signals, a further processing means 34-*f* for processing the combined amplified and filtered detection signals, wherein this processing may comprise envelope extraction and thresholding, and a decision means 34-*e*. Processing of the combined amplified and filtered detection signals may be similar to the processing of the amplified and filtered detection signal described with reference to FIG. 2. The two sensor means can be an accelerometer and/or an acoustic sensor.

The configuration comprising more than one sensor means (33-*a*, 33-*b*) shown in FIG. 3 may provide some advantages with respect to the configuration comprising one sensor means (23) shown in FIG. 2. On the other hand, complexity is increased when more than one senor means is provided. In the configuration shown in FIG. 3 a quality factor of the detection signals (for example the ratio between the baseline noise and the peaks) obtained by the sensor means 33-*a* and 33-*b* may be determined and based on the determination result only one of detection signals or combined parts of the detection signals may be further processed. In this way, the device might improve its resilience with respect to possible differences in coupling of the accelerometers with the mechanical vibrations, due for example to the lead position in the patient body or to varying patient to patient characteristics. The device might, instead of simply cutting off one or more sensor means, combine the separate signals in one signal via, for example, a correlation process, whereby the resulting signal is proportional to the level of correlation between the two or more individual accelerometer. This might allow to better discriminate between the actual cardiac signal and noises of foreign origin, which might appear in one of the sensor means but not in the others.

Figure 4:
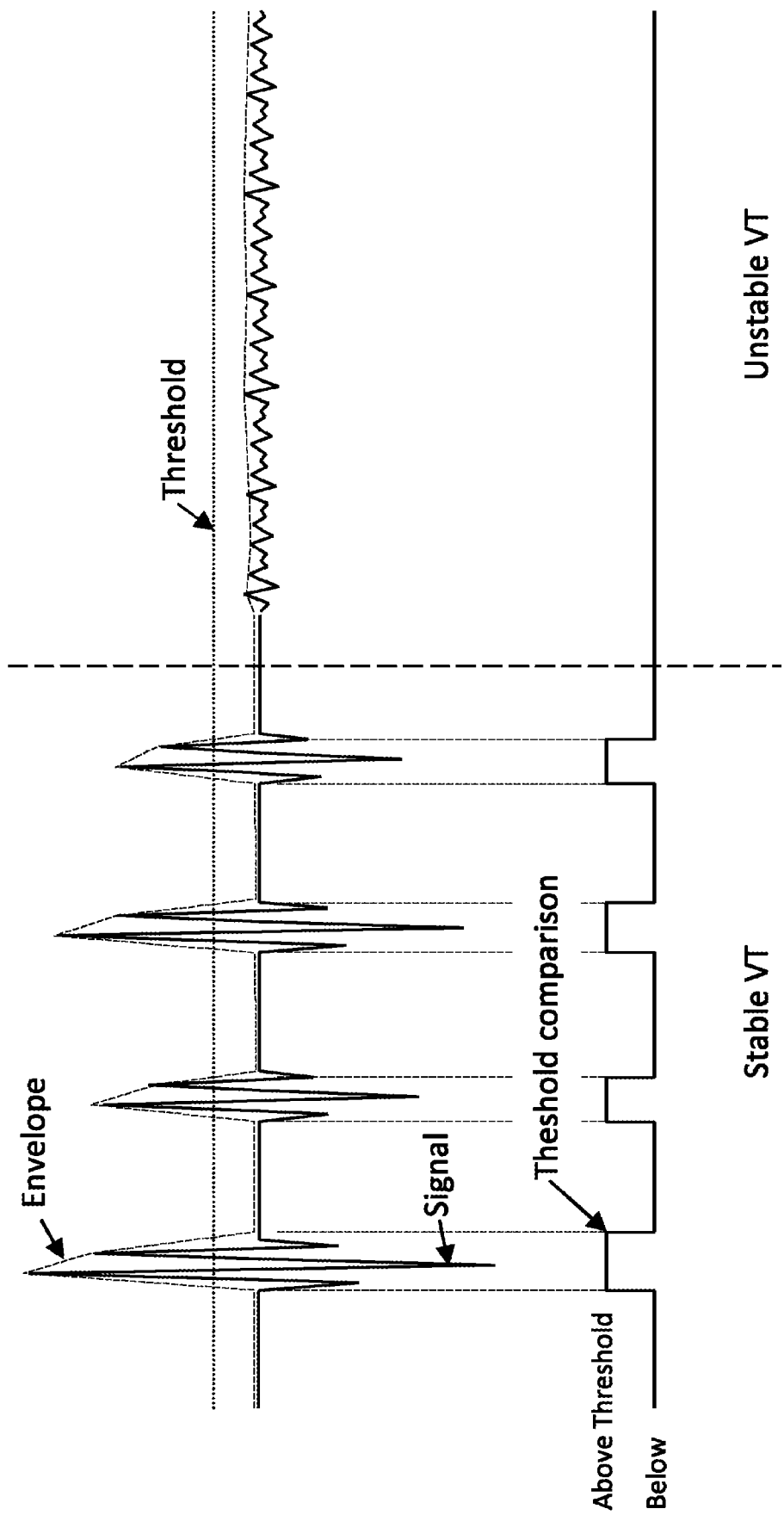
FIG. 4 illustrates envelope extraction and thresholding in the context of the analysis of a detection signal.

As already described in both the configuration shown in FIG. 2 and the configuration shown in FIG. 2 an envelope of (combined) detection signal can be extracted. FIG. 4 illustrates an envelope (dashed line) of a detection signal. The signal can be compared with a threshold. The result of the comparison is shown in the lower part of FIG. 4 in binary representation ("0" for envelope does not exceed threshold, "1" for envelope exceeds threshold). Thereby, stable VT can reliably be distinguished from unstable VT (envelope below threshold) that requires activation of the defibrillator 20, 30.

In the embodiments shown in FIGS. 2 and 3, the sensor means 23 or 33*a*, 33*b* are positioned in the lead, so that in use it will be in or close to the heart. According to variants, the sensor means could be arranged separately from the lead, e.g. positioned in the housing of the defibrillator unit 20, 30 comprising the controller 21, 31. According to a further variant, the sensor means could also be a non-implantable sensor means, e.g. incorporated into a patch or fixable by an adhesive tape.

Figure 5:
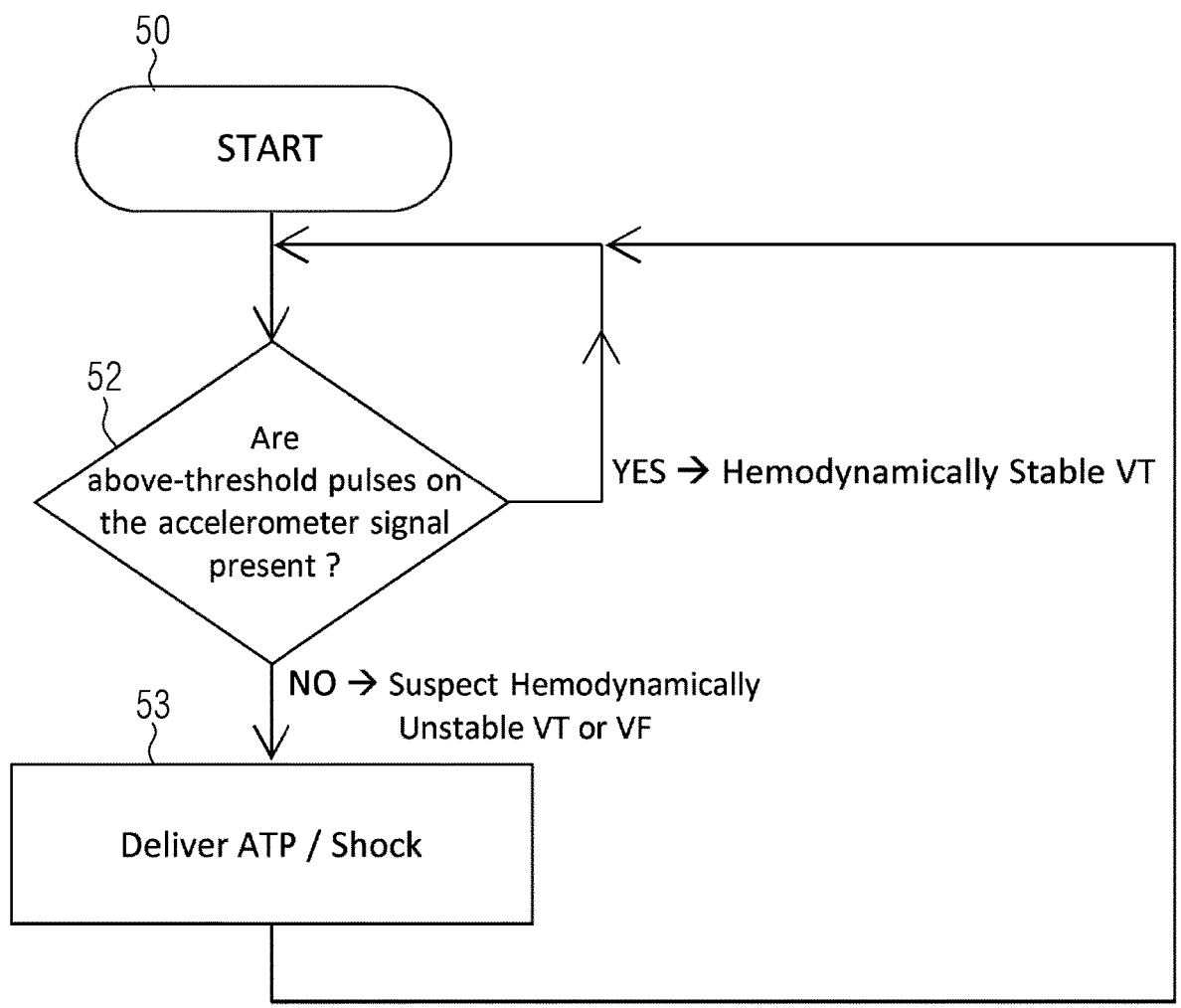
FIG. 5 is a flow chart illustrating operation of an implantable device according to an exemplary embodiment.
Figure 6:
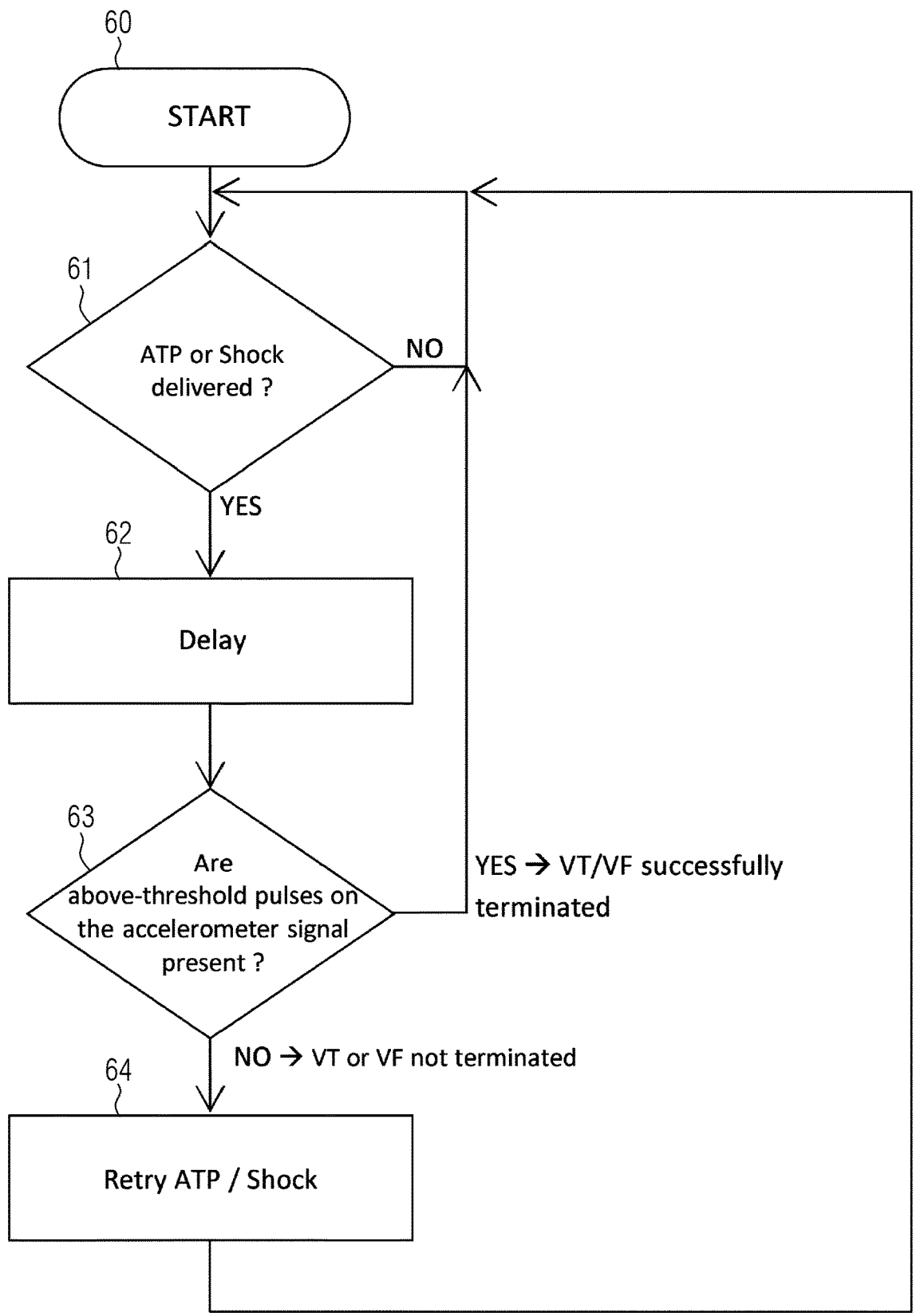
FIG. 6 is a flow chart illustrating operation of an implantable device according to another exemplary embodiment.

Exemplary operation modes of the devices shown in FIGS. 2 and 3 are illustrated in FIGS. 5 and 6. The process flow illustrated in FIG. 5 starts at 50. In the shown example, a decision on whether or not an electrical shock is to be delivered is made based on an accelerometer or acoustic sensor signal, or any other detection signal obtain by a sensor means detecting a heart sound, see 23 and 33-a and 33-b of FIGS. 2, and 3, respectively In step 52 it is determined whether or not the accelerometer or acoustic signal or any other detection signal obtained by a sensor means detecting a heart sound or the envelope of it exceeds a predetermined threshold; see also description of FIGS. 2 to 4. If it is determined that significant pulses are present, thus the threshold is exceeded (YES), it is assumed that hemodynamically stable VT is present and nothing special happens. If it is determined that the threshold is not exceeded by the detection signal or the envelope of the same (NO), it is assumed that hemodynamically unstable VT or VF are present and the decision means described with reference to FIGS. 2 and 3 decides that the defibrillator 20, 30 has to deliver 53 an electrical shock in order to terminate the assumed hemodynamically unstable VT or VF.

Another operation mode of the devices shown in FIGS. 2 and 3 is shown in FIG. 6. The procedure starts at 60. At 61 it is determined whether a therapeutic electric defibrillation signal is delivered to a patient. Deliverance of this therapeutic electric defibrillation signal can be decided as described with reference to FIG. 5, for example. After the therapeutic electric defibrillation signal has been delivered (YES), optionally, it is waited 61 for a predetermined time period in order to allow for normal cardiac rhythm to be restored.

In step 63 (similar to step 52 of FIG. 5) it is determined whether or not the accelerometer or acoustic sensor signal (or any other detection signal obtained by a sensor means detecting a heart sound) or the envelope of it exceeds a predetermined threshold. If that signal or the envelope of it is above the predetermined threshold (YES), indicating a periodic opening and closing of the valves in response to the previously delivered therapeutic electric defibrillation signal, unstable VT or VF may be declared as successfully having been terminated and the algorithm can go in a standby state waiting for the next event to come, for example. If, on the contrary, that signal lies below the threshold (NO), an unsuccessful termination of the VT or VF might be assumed. In this case, another therapeutic electric defibrillation signal (electrical shock) may be delivered to the patient.

All previously discussed embodiments are not intended as limitations but serve as examples illustrating features and advantages of the invention. It is to be understood that some or all of the above described features and embodiments can also be combined in different ways.

What is claimed is:

1. An implantable medical device comprising:
   an implantable defibrillator configured to generate an electrical defibrillation signal;
   an implantable electrode connected to the implantable defibrillator by a lead and configured to deliver the electrical defibrillation signal to a patient;
   an implantable sensor configured to detect mechanical vibrations by the heart of the patient and to provide a detection signal based on the detected mechanical vibrations; and
   a controller configured to analyze the detection signal to determine at least one parameter characterizing the mechanical vibrations and to provide a defibrillation operation of the implantable defibrillator, the defibrillation operation based only on the determined parameters characterizing the mechanical vibrations.

2. The implantable medical device according to claim 1, wherein the determined parameter is at least one of amplitude, correlation, autocorrelation, morphology or a presence of doublets in the detected signal.

3. The implantable medical device according to claim 1, wherein the sensor is positioned in the lead or in a housing comprising the controller.

4. The implantable medical device according to claim 1, wherein the controller is configured to cause the defibrillator to deliver the electrical defibrillation signal to the patient in response to the parameter characterizing the mechanical vibrations being below a predetermined threshold.

5. The implantable medical device according to claim 1, wherein the sensor comprises one or more of an accelerometer, such that the detection signal is an accelerometer signal, or an acoustic sensor, such that the detection signal is an acoustic signal.

6. The implantable medical device according to claim 5, wherein the sensor comprises an accelerometer and the detection signal is an accelerometer signal, and wherein the controller is configured to cause the defibrillator to deliver the electrical defibrillation signal to the patient in response to an extracted envelope of the accelerometer signal being below a predetermined threshold.

7. The implantable medical device according to claim 1, further comprising at least one additional sensor, the additional sensor positioned in the lead and configured to detect a heart sound to obtain an additional detection signal.

8. The implantable medical device according to claim 7, wherein the sensor and the additional sensor means are positioned in the lead at different locations, and wherein the controller is configured to control the operation of the defibrillator based on the additional detection signal obtained by the additional sensor.

9. The implantable medical device according to claim 8, wherein the controller is configured to determine a correlation between the detection signal and the additional detection signal or a signal to noise ratio of the detection signal and the additional detection signal as a parameter characterizing the mechanical vibrations.

10. The implantable medical device according to claim 1, wherein the controller is configured to analyze the detection signal obtained after a first electrical defibrillation signal has been delivered and to control operation of the implantable defibrillator based on the detection signal such that a second electrical defibrillation signal is delivered or not based on the analyzed detection signal.

11. An implantable medical device comprising:
   an implantable defibrillator configured to generate an electrical defibrillation signal;
   an implantable electrode connected to the implantable defibrillator by a lead and configured to deliver the electrical defibrillation signal to a patient;
   an implantable sensor configured to detect mechanical vibrations of the heart of the patient, and to provide a detection signal based on the detected mechanical vibrations; and a controller configured to analyze the detection signal to determine at least one parameter characterizing the mechanical vibrations, and provide a defibrillation operation based on the determined parameters characterizing the mechanical vibrations without analyzing any other detection signal.

* * * * *